US007748381B2

(12) United States Patent
Croll et al.

(10) Patent No.: US 7,748,381 B2

(45) Date of Patent: Jul. 6, 2010

(54) PORTABLE BLOWER SYSTEM

(75) Inventors: Lisa M. Croll, Brockville (CA); Pierre Legare, Brockville (CA); David E. Livingstone, Harrietsville (CA)

(73) Assignee: 3M Innovative Properties Company, St. Paul, MN (US)

( * ) Notice: Subject to any disclaimer, the term of this patent is extended or adjusted under 35 U.S.C. 154(b) by 1207 days.

(21) Appl. No.: 11/275,087

(22) Filed: Dec. 9, 2005

(65) Prior Publication Data

US 2007/0131228 A1 Jun. 14, 2007

(51) Int. Cl.
*A61M 11/00* (2006.01)

(52) U.S. Cl. ................................ 128/204.18; 415/55.4

(58) Field of Classification Search ............ 128/204.15, 128/204.21, 206.17, 205.12, 205.27, 205.29, 128/201.25, 204.18; 415/55.4; 416/185, 416/186 R, 223 B, 243

See application file for complete search history.

(56) References Cited

U.S. PATENT DOCUMENTS

| | | | |
|---|---|---|---|
| 4,236,902 | A | 12/1980 | Fricke |
| 4,401,151 | A | 8/1983 | Pozsicsányi |
| 5,266,007 | A | 11/1993 | Bushnell et al. |
| 5,616,011 | A | 4/1997 | Witschi |
| 6,357,249 | B1 | 3/2002 | Robinson et al. |
| 6,575,165 | B1 | 6/2003 | Cook et al. |
| 6,632,071 | B2 | 10/2003 | Pauly |
| 6,868,821 | B2 | 3/2005 | Maier et al. |
| 6,880,516 | B2 | 4/2005 | Maier et al. |
| 6,886,615 | B2 | 5/2005 | Wixey et al. |
| 6,918,419 | B2 | 7/2005 | Wixey et al. |
| 2002/0119044 | A1 | 8/2002 | O'Connor, Jr. et al. |
| 2005/0089409 | A1 | 4/2005 | Boohar et al. |
| 2005/0197684 | A1 | 9/2005 | Koch |
| 2005/0207883 | A1 | 9/2005 | Shufeldt |

FOREIGN PATENT DOCUMENTS

| | | | |
|---|---|---|---|
| CN | 152507 | A | 9/2004 |
| CN | 2702097 | Y | 5/2005 |
| EP | 0 387 283 | B1 | 10/1988 |
| EP | 0 198 654 | B1 | 1/1991 |
| EP | 1 095 233 | B1 | 7/1999 |
| EP | 1 355 064 | B1 | 4/2002 |
| EP | 1 510 291 | A1 | 8/2004 |
| EP | 1 537 818 | A2 | 12/2004 |

(Continued)

OTHER PUBLICATIONS

Physiological Efficacy of a Lightweight Ambient Air Cooling Unit for Various Applications (Armstrong Lab., Brooks AFB, TX); U.S. Dept. Of Commerce National Technical Information Service Publication # ADA272952; Oct. 1993; 14 pgs.

(Continued)

*Primary Examiner*—Steven O Douglas
(74) *Attorney, Agent, or Firm*—Anna A. Wetzels

(57) ABSTRACT

A portable cooling or respiratory blower system of the type carried by a user's body includes a housing having two air flow chambers. An impeller is rotatably disposed between the two air flow chambers and includes a base wall that places the two air flow chambers in non-fluidic communication when the impeller is rotated. A separate plurality of blades is provided on each side of the base wall.

19 Claims, 5 Drawing Sheets

FOREIGN PATENT DOCUMENTS

EP 1 564 869 A2 12/2004

OTHER PUBLICATIONS

Howden Power Ltd. Customers Manual; Product Information Howden Centrifugal Fan; Howden Power Ltd.; Old Govan Road, Renfrew, UK; PA4 8XJ; www.howden.com; Jul. 20, 2000; 5 pgs.

Development of a Personal Cooling System for Explosive Ordnance Disposal Personnel (Army Natick Labs Mass. Clothing & Personal Life Support Equipment Lab); U.S. Dept. of Commerce National Technical Information Service Publication # AD702245; Dec. 1969; 17 pgs.

Portable, Ambient Air Microclimate Cooling in Simulated Desert and Tropic Conditions (Army Research Institute of Environmental Medicine, Natick, MA); U.S. Dept. of Commerce National Technical Information Service Publication # ADA186457; Apr. 1987; 21 pgs.

PORTABLE BLOWER SYSTEM

BACKGROUND

The present disclosure relates to blower systems.

Current portable air moving systems are utilized in a variety of different applications. One particular application involves Powered Air Purifying Respirators (PAPR). PAPRs are generally used in industrial applications where environmental hazards are well defined and quantified. Respiratory hazards might include harmful gases, vapors and particulate matter. Currently, PAPRs include a battery-powered blower unit having at least one attached filter and a breathing mask or other suitable hood, helmet or headtop, having an inlet for receiving air from the blower unit. PAPRs are employed to continually supply positive air pressure to a user's mask or hood of a protective suit. Ambient air, from the environment in which the PAPR is located, is drawn through the filter(s) and supplied to the mask, hood or full body suit by the blower. The filtered supplied air replenishes the internal confines of the mask or hood, and is continually ejected as the user breathes.

Another application for portable air moving systems includes ambient air cooling systems. These cooling systems are generally borne by a user and supply air flow to and around a user's body. In situations where a user is in a hot area burdened with large amounts of clothing and/or equipment, a cooling system is desirable in order to provide cooling to the body. These cooling systems require a sufficient amount of air flow in order to achieve a desired performance for heat removal from the body. In these applications, air flow delivery, efficiency and battery longevity are desired in a compact, lightweight design.

SUMMARY

In one aspect, the present invention presents a portable cooling or respiratory blower system of the type carried by a user's body includes a housing having two air flow chambers. An impeller is rotatably disposed between the two air flow chambers and includes a base wall that places the two air flow chambers in non-fluidic communication when the impeller is rotated. A separate plurality of blades is provided on each side of the base wall.

This summary is not intended to describe each disclosed embodiment or every implementation of the present invention. The Figures and the description that follows more particularly exemplify illustrative embodiments.

BRIEF DESCRIPTION OF THE DRAWINGS

The present invention will be further explained with reference to the attached figures, wherein like structure or system elements are referred to by like reference numerals throughout the several views.

While the above-identified figures set forth one or more embodiments of the present invention, other embodiments are also contemplated, as noted in the disclosure. In all cases, this disclosure presents the invention by way of representation and not limitation. It should be understood that numerous other modifications and embodiments can be devised by those skilled in the art which fall within the scope and spirit of the principles of this invention.

GLOSSARY

The terms set forth below will have the meanings as defined:

"air exchange apparatus" means an apparatus for providing a finite breathing zone volume around the head of a user in which air can be exchanged in conjunction with the user's breathing cycle.

"air flow" means a non-zero degree of air movement.

"air inlet" means one or more air entry points.

"air outlet" means one or more air exit points.

"ambient air" means air present in a given environment independent of any air cleaning or air moving apparatus present in that environment.

"ambient air cooling system" means a powered system for delivering air flow to a particular area.

"backward inclined blades" means that blades are inclined in an opposite direction to a direction of rotation for an impeller.

"blower" means a device for generating air flows.

"clean air" means air that has been filtered or that otherwise has been made safe to breath or to be in contact with skin.

"common air source" means a supply of air that is shared by at least two air inlets.

"impeller" means a rotating device used to force a fluid in a desired direction under pressure.

"non-fluidic communication" means that no appreciable amount of fluid is exchanged between two chambers.

"portable" means capable of being used while in motion and without direct connection to a fixed object.

"Powered Air Purifying Respirator" (PAPR) means a powered system for forcing clean air into the air exchange apparatus by driving ambient air through an air filter.

"scroll" means an annulus having a constantly increasing diameter.

DETAILED DESCRIPTION

Figure 1:
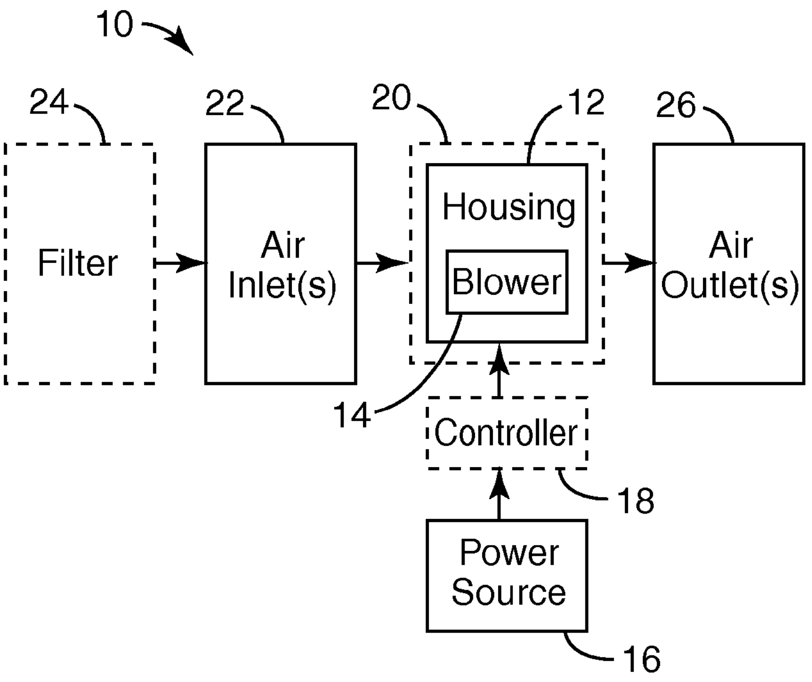
FIG. 1 is a schematic diagram of a portable blower system.

FIG. 1 is a schematic diagram of a portable blower system 10. System 10 includes a housing 12 having a blower 14 disposed therein. Blower 14 is electrically coupled to a power source 16. If desired, a controller 18 can be used to control power provided to blower 14. Controller 18 can include a simple on/off switch and/or other sophisticated elements, such as a constant flow control via feedback control or pulse width modulation of motor output. Controller 18 can also optionally incorporate visual and/or audible alarms based on various parameters, such as low air flow, low battery or any out of standard operating state. Alternatively, power source 16 can provide power directly to blower 14. An optional outer body 20 is provided to enclose the housing 12 and provide a common air source thereto. In one embodiment, body 20 can also be configured to further enclose power source 16 and/or controller 18.

Blower 14 is used to create negative pressure in a chamber within housing 12, which draws air through one or more air inlets, collectively referred to as air inlet 22. Air inlet 22 can optionally be coupled to air treatment media such as a filter 24 to filter environmental hazards such as harmful gases, vapors and particulate matter. Or, for example, an ambient air cooling system may include a filter to remove contaminants such as sand from air inlet 22. Blower 14 delivers air to one or more air outlets, collectively referred to as air outlet 26. Air outlet 26 can include a tube to facilitate air flow to a head gear worn by a user or to a user's body, for example. Air outlet 26 can also be configured to supply air to multiple devices, such as to both the head gear and the cooling vest.

Figure 3:
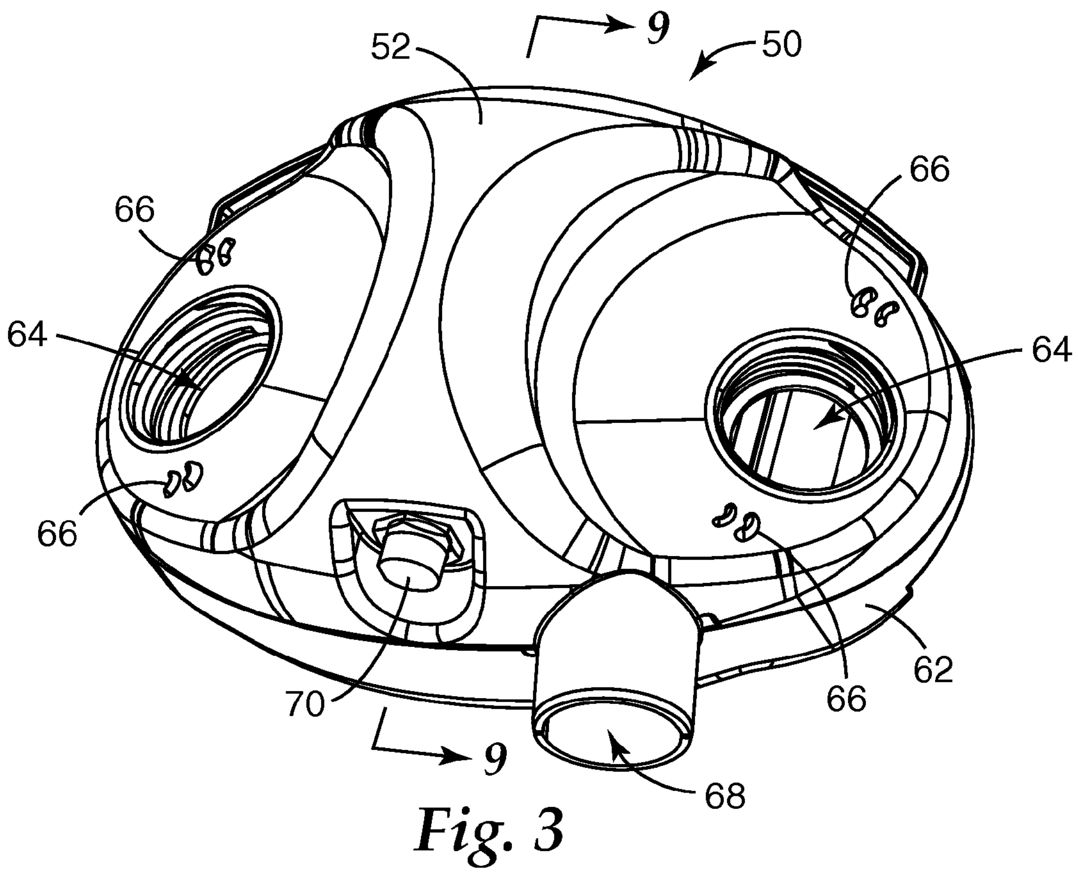
FIG. 3 is an isometric view of a portable blower system.
Figure 2:
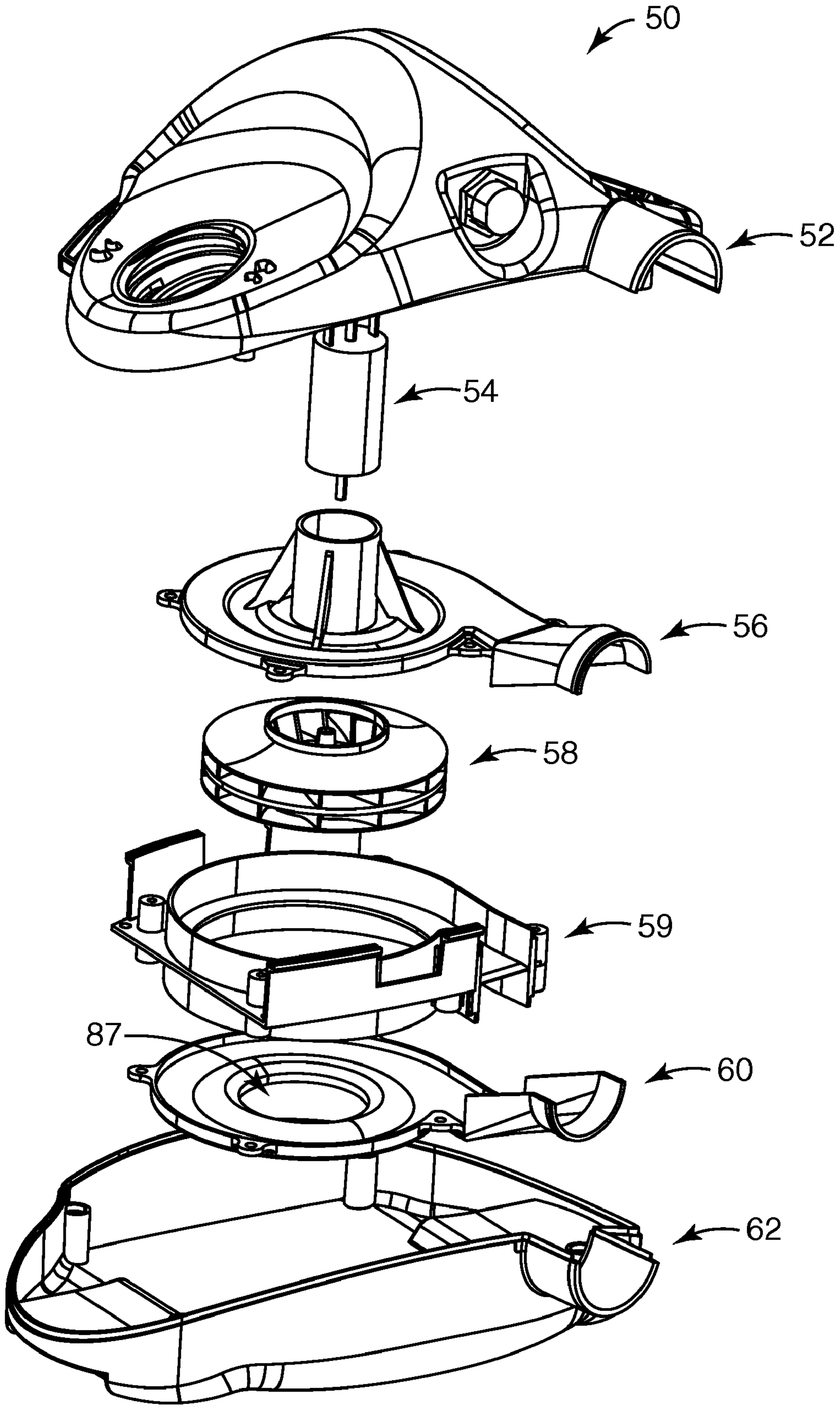
FIG. 2 is an exploded perspective view of components in a portable blower system.

FIGS. 2-9 illustrate a blower system 50. FIG. 2 is an exploded isometric view of components in blower system 50. Blower system 50 includes an outer body top cover 52, a motor 54, a scroll housing top cover 56, an impeller 58, a scroll housing frame 59, a scroll housing bottom cover 60 and an outer body bottom cover 62. FIG. 3 is an isometric view of the components in FIG. 2 assembled in system 50. Outer body top cover 52 and outer body bottom cover 62 form an outer body to enclose the motor 54, scroll housing top cover 56, impeller 58, scroll housing frame 59 and scroll housing bottom cover 60. The outer body supplies a common air source to impeller 58.

Outer body top cover 52 and outer body bottom cover 62 can be molded from a resin resistant to a chemical biological ("CB") agent exposure. One example resin is available under the trademark NORYL®, and provided by General Electrical Company of Fairfield, Conn. NORYL® resin is a co-polymer mixture of polyphenlyene oxide and polystyrene resins. Other resins may also be suitable for outer body top cover 52 and outer body bottom cover 62. Furthermore, outer body top cover 52 and outer body bottom cover 62 can be sealed wherein outer body top cover 52 includes a projection that is positioned within a V-shaped groove of outer body bottom cover 62 and including a suitable sealant, for example, caulk or polyurethane, therebetween.

Outer body top cover 52 includes air intake portions 64. As illustrated, intake portion 64 can include threaded attachment ports and associated detents 66 for attaching filters thereto. An air outlet 68 is provided for pressurized air delivery output from system 50. Air outlet 68 can extend from the outer body top cover 52 and outer body bottom cover 62 to allow a hosing to attach thereto. If desired, a coupling designed to facilitate hose removal and replacement can be combined with air outlet 68. The hosing can also be CB resistant, for example by using a butyl rubber formulation. A spiral wrap hosing configuration can be utilized for reducing air flow resistance and imparting crush resistance of the hosing.

An electrical connector 70 is provided on outer body top cover 52. Electrical connector 70 can be electrically coupled to a power source such as a battery and coupled to circuitry and/or a motor within system 50.

Figure 4:
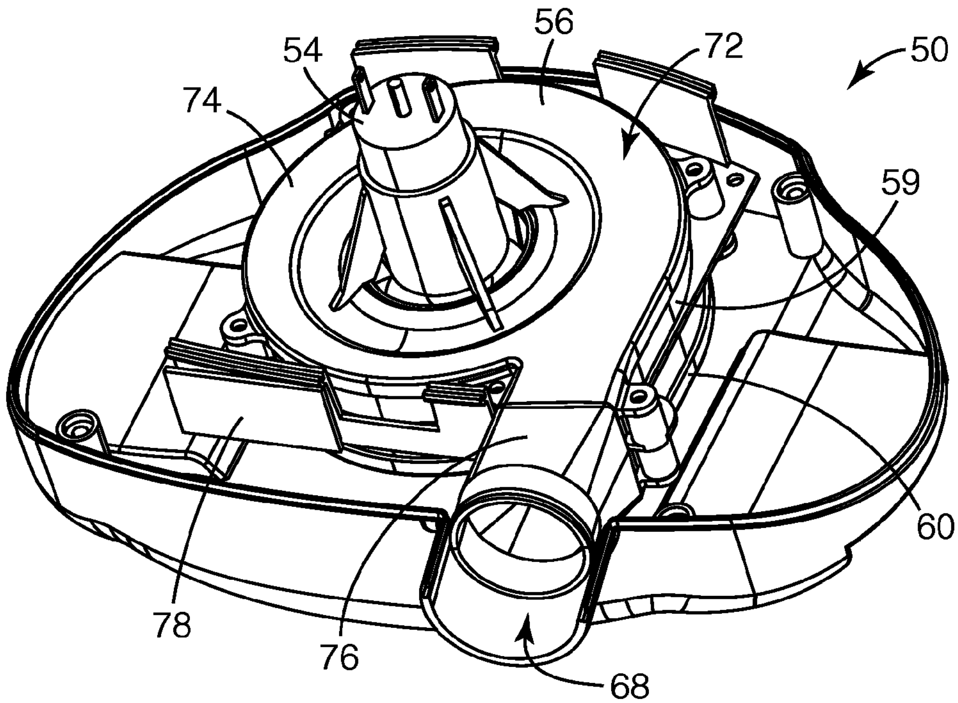
FIG. 4 is an isometric view of the portable blower system of FIG. 3 with an outer body top cover removed.

FIG. 4 is an isometric view of system 50 with outer body top cover 52 removed. Scroll housing top cover 56, scroll housing frame 59 and scroll housing bottom cover 60 collectively form scroll housing 72 that is positioned in outer body bottom cover 62. Scroll housing 72 includes an annular member 74 coupled to an outlet 76. Outlet 76 is aligned with air outlet 68 formed by outer body top cover 52 and outer body bottom cover 62. Electronic circuitry 78 and be coupled to scroll housing frame 59. Electrical circuitry 78 can be coupled to electrical connector 70 (FIG. 3) and electrically coupled to motor 54 to provide a drive thereto. The electrical circuitry 78 may serve as the controller 18 (FIG. 1) in one embodiment.

Figure 5:
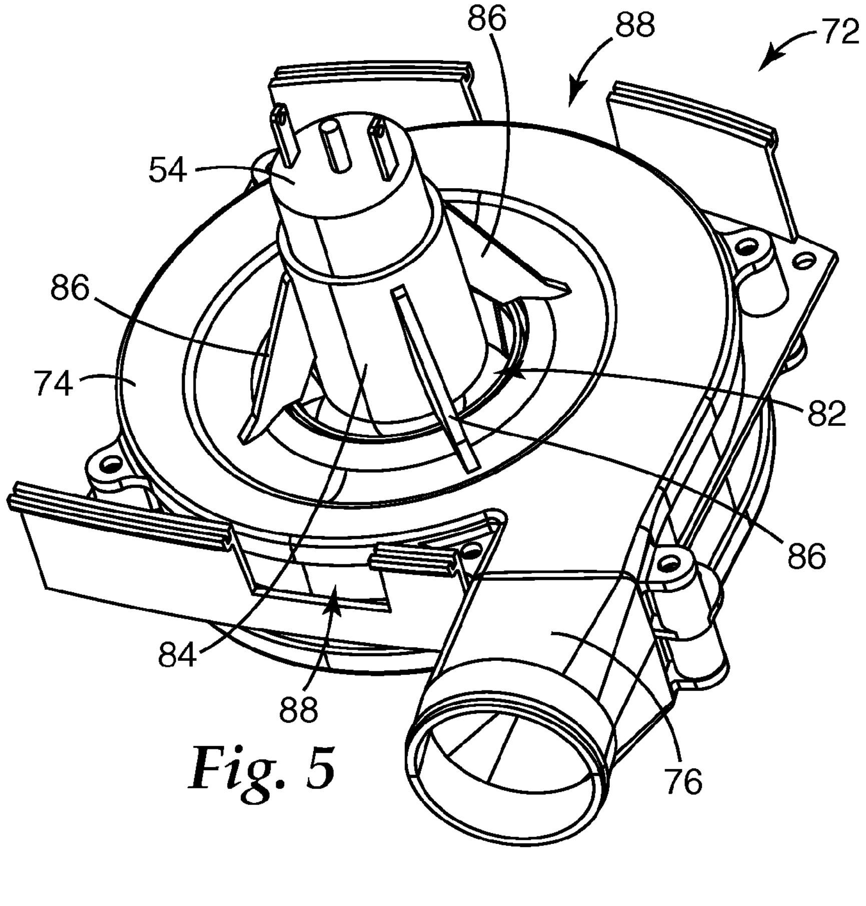
FIG. 5 is an isometric view of a scroll housing.

FIG. 5 is an isometric view of scroll housing 72. Motor 54 includes a drive axis that is offset with respect to a central axis of annual member 74. Motor 54 is positioned above an inlet 82 in scroll housing top cover 56. A motor mount 84 includes a plurality of gussets 86 to support motor 54 above inlet 82. Scroll housing bottom cover 60 also includes an inlet (see 87 in FIG. 2) to allow air flow into scroll housing 72. Scroll housing top cover 56 forms a first wall, scroll housing bottom cover 60 forms a second wall, and scroll housing frame 59 forms a third wall that, in combination with the first and second walls, define a chamber between the impeller and the walls of the scroll housing 72. Air passageways 88 are provided in scroll housing frame 59 to facilitate air flow around the outside of scroll housing 72 within the outer body top and bottom covers 52 and 62, and, in particular to inlets 82 and 87 in scroll housing top cover 56 and scroll housing bottom cover 60, respectively.

Figure 6:
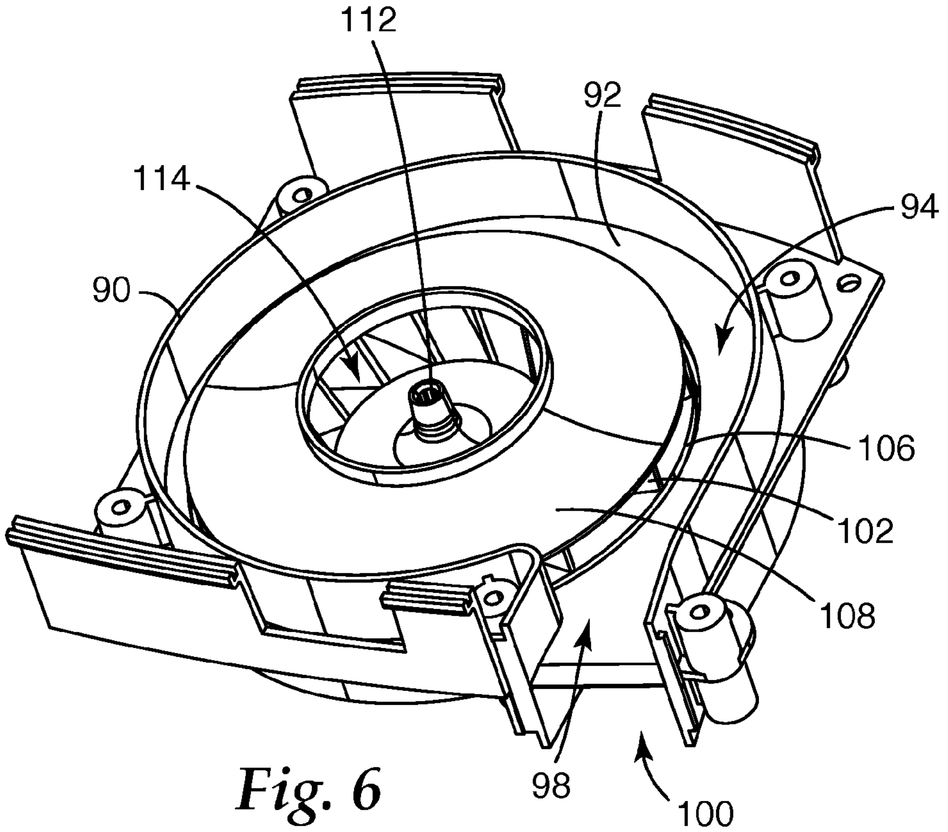
FIG. 6 is an isometric view of a scroll housing frame and an impeller.
Figure 7:
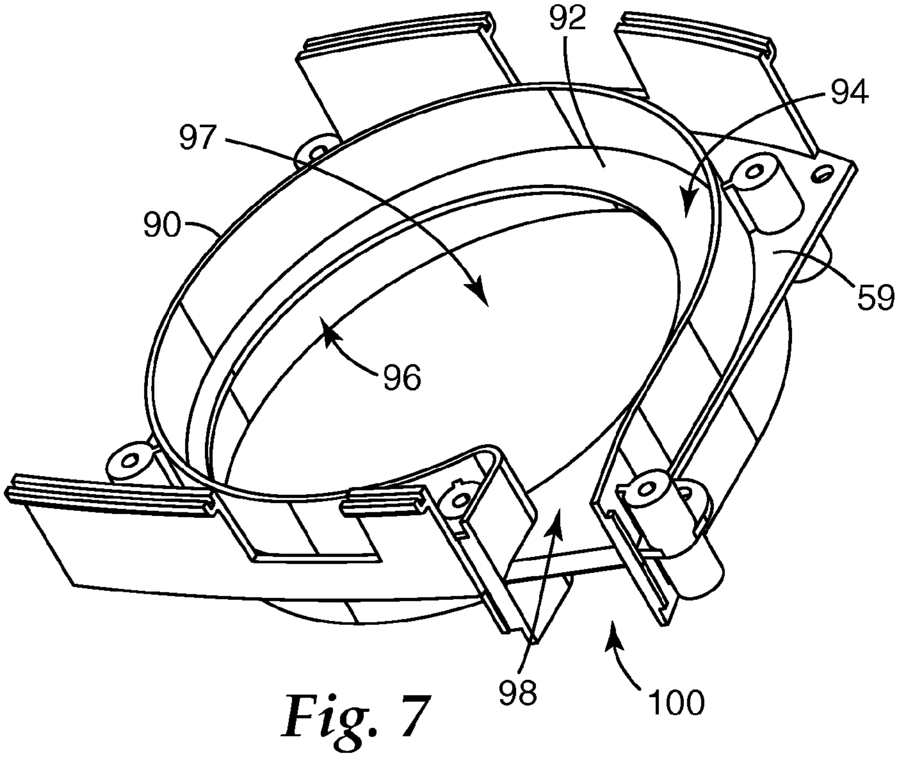
FIG. 7 is an isometric view of the scroll housing frame of FIG. 6.
Figure 8:
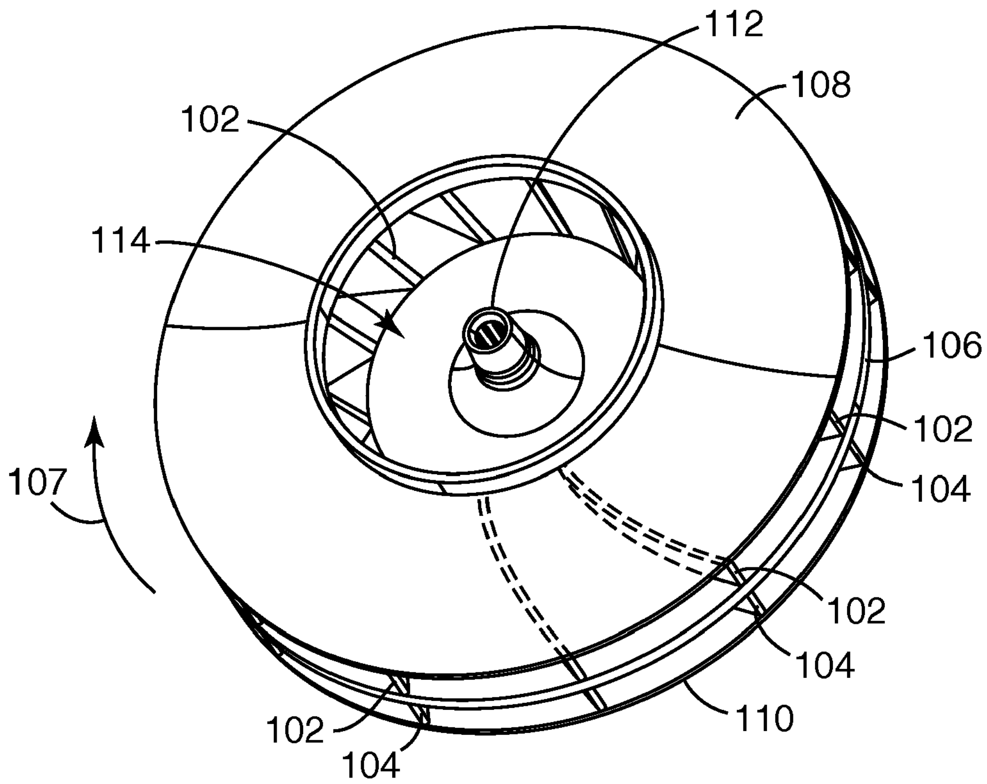
FIG. 8 is an isometric view of the impeller of FIG. 6.

FIG. 6 is an isometric view of impeller 58 positioned for rotation within scroll housing frame 59. FIG. 7 is an isometric view of scroll housing frame 59 alone and FIG. 8 is an isometric view of impeller 58 alone. Scroll housing frame 59 includes a circumferential wall 90 and an axially extending dividing wall 92. Dividing wall 92 extends inwardly from wall 90 toward an outer circumferential edge of impeller 58. Dividing wall 92 creates, in part, a first air flow chamber 94 and a second air flow chamber 96 on each side of the wall, and has a circular opening 97 therethrough. Chambers 94 and 96 include outer generally annular plenums on either side of dividing wall 92 that are fluidly coupled to air outlets 98 and 100, respectively. Air outlets 98 and 100 extend through wall 90 of scroll housing frame 59. Impeller 58 is axially offset with respect to a center of scroll housing frame 59 and fits within circular opening 97 in dividing wall 92. To accommodate the offset, dividing wall 92 is non-uniform in radial width, to allow non-fluidic communication between chambers 94 and 96 when the impeller 58 is in place for rotation (FIG. 6) and is rotating.

Impeller 58 is a two-sided impeller, and includes a first set of blades 102 and a second separate set of blades 104 positioned on either side of a circular impeller dividing wall 106. First set of blades 102 and second set of blades 104 can be "backward inclined," meaning that the blades are inclined in an opposite direction to a direction of rotation for impeller 58 (indicated in FIG. 8 by arrow 107). In one embodiment, first set of blades 102 and second set of blades 104 are formed as mirror images on opposite faces of dividing wall 106, although other orientations for the blades can also be used. Dividing wall 106, when positioned within circular opening 97 of the dividing wall 92 of the scroll housing 72, is coplanar with dividing wall 92 of scroll housing frame 59. Impeller 58 further includes a top arcuate wall 108 and a bottom arcuate wall 110 (seen in FIG. 9). A central hub 112 of impeller 58 is rotatably coupleable to motor 54 to drive impeller 58. Intakes 114 and 116 (FIG. 9) are provided on either side of impeller 58.

Figure 9:
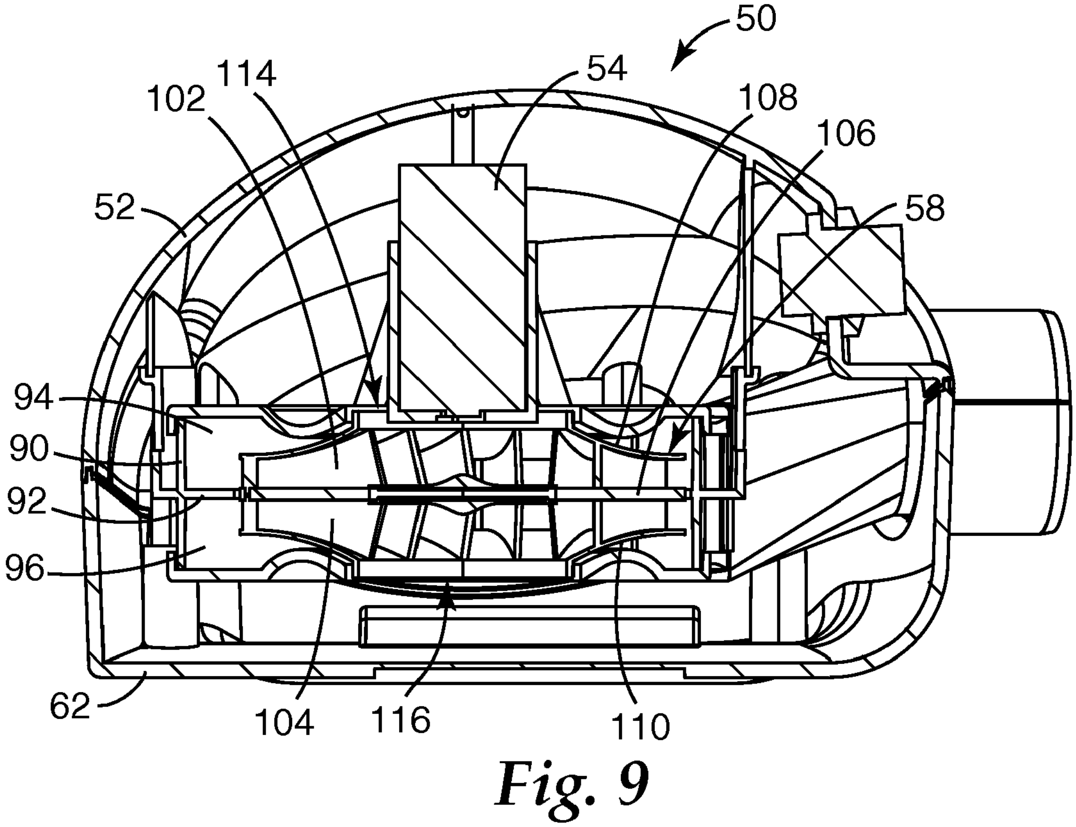
FIG. 9 is a cross-sectional view of the portable blower system of FIG. 3.

With further reference to FIG. 9, motor 54 causes impeller 58 to rotate. During operation, air flows from the outside the outer body top and bottom covers 52 and 62 (through intake portions 64), around scroll housing 72 and into inlets 82 and 87 in the scroll housing top and bottom covers. In one embodiment, air drawn into the impeller is conditioned before reaching the impeller by passage through a treatment medium (e.g. filter material, charcoal, thermally treated, ionized, etc.). Air then flows into impeller intakes 114 and 116. First set of blades 102 force air from intake 114 into chamber 94, in particular its outer plenum. Similarly, second set of blades 104 forces air from intake 116 in to chamber 96, in particular its outer plenum. Air is then forced from chambers 94 and 96 to outlets 98 and 100, respectively. During impeller rotation, dividing wall 92 of scroll housing frame 59 and dividing wall 106 of impeller 58 keep chambers 94 and 96 in non-fluidic communication. Although a small radial clearance gap (e.g., less than 1 mm) exists between dividing wall 92 and dividing wall 106, no appreciable amount of fluid transfers between chambers 94 and 96.

Although the present invention has been described with reference to several alternative embodiments, workers skilled in the art will recognize that changes may be made in form and detail without departing from the spirit and the scope of the invention. For instance, air outlets 98 and 100 of chambers 94 and 96 may be in fluid communication (as shown) at air outlet 68, or may be connected to separate air outlets (e.g., one for use for providing air for breathing and the other for providing air for cooling). In addition, while the blower system of the present invention is illustrated in connection with portable cooling or respiratory blower systems of the type carried by a user's body, the invention can be used in a variety of types of air moving applications (e.g., vehicle fan systems, HVAC systems, vacuum cleaners, etc.). Moreover, features shown and described with respect to one embodiment may be combined with features of other embodiments, as desired.

What is claimed is:

1. A portable cooling or respiratory blower system of the type carried by a user's body, the blower system comprising:

a housing having two air flow chambers; and an impeller rotatably disposed between the two air flow chambers, the impeller having a base wall that places the two air flow chambers in non-fluidic communication when the impeller is rotated, and the impeller having a separate plurality of blades on each side of the base wall.

2. The blower system of claim 1 wherein each chamber of the housing has an air inlet in fluid communication with a common air source.

3. The blower system of claim 2, and further comprising:

an outer body enclosing the housing to supply the common air source.

4. The blower system of claim 2, and further comprising:

air treatment media disposed relative to each air inlet of the housing such that air entering the housing must traverse the air treatment media before it enters the air flow chambers in the housing.

5. The blower system of claim 1, and further comprising:

a motor borne by the housing and operably attached to the impeller for rotating the impeller.

6. The blower system of claim 1, wherein each chamber has an air outlet.

7. The blower system of claim 6, wherein the air outlets of the two housing chambers are in fluid communication.

8. The blower system of claim 6, wherein each air flow chamber has a plenum which extends radially beyond the impeller, with each plenum being in fluid communication with the air outlet for its respective air flow chamber.

9. The blower system of claim 8, wherein each of the plenums is generally annular.

10. The blower system of claim 1, wherein the housing has a radially extending dividing wall which cooperates with the base wall of the impeller to place the two air flow chambers in non-fluidic communication when the impeller is rotating.

11. The blower system of claim 1 wherein the impeller includes a top wall having an arcuate surface and a bottom wall having an arcuate surface.

12. The blower system of claim 11 wherein the top wall includes a central air intake and the bottom wall includes a central air intake.

13. In a portable cooling or respiratory blower system of the type carried by a user's body, the improvement which comprises:

an impeller rotatable about an axis, the impeller comprising:

a circular dividing wall wherein the wall has first and second opposite faces and an outer circumferential edge, a first plurality of blades on the first face of the wall, and a second, separate plurality of blades on the second face of the wall; and an impeller housing non-rotatably disposed about the impeller, the impeller housing comprising:

a first wall having an air inlet, a second wall having an air inlet, a third wall spaced from the outer circumferential edge of the dividing wall of the impeller to define, in combination with portions of the first and second walls of the housing, a chamber between the impeller and the walls of the housing, a dividing wall extending inwardly from the third wall of the housing toward the outer circumferential edge of the dividing wall of the impeller, wherein the dividing wall of the housing extends generally co-planar with the dividing wall of the impeller and is formed to separate the chamber into first and second outlet plenums, and at least one air outlet for each outlet plenum that extends through one or more of the walls of the housing.

14. The improvement of claim 13, and further comprising:

air treatment media disposed relative to each air inlet of the housing such that air entering the housing must traverse the air treatment media before it enters the housing.

15. The improvement of claim 13, and further comprising:

a motor borne by the housing and operably attached to the impeller for rotating the impeller.

16. The improvement of claim 13, wherein the housing has a first air outlet for the first outlet plenum and a second, separate air outlet for the second outlet plenum.

17. The improvement of claim 13, wherein the at least one air outlet of the housing is in fluid communication with both the first and second outlet plenums.

18. The improvement of claim 13, wherein the air inlets of the housing are in fluid communication with a common air source.

19. The improvement of claim 13 wherein the impeller includes a top wall having an arcuate surface and a bottom wall having an arcuate surface.

* * * * *

UNITED STATES PATENT AND TRADEMARK OFFICE

CERTIFICATE OF CORRECTION

PATENT NO. : 7,748,381 B2
APPLICATION NO. : 11/275087
DATED : July 6, 2010
INVENTOR(S) : Lisa Marie Croll It is certified that error appears in the above-identified patent and that said Letters Patent is hereby corrected as shown below:

Column 3
Line 29, delete "polyphenlyene" and insert -- polyphenylene --, therefor.

Signed and Sealed this

Nineteenth Day of October, 2010

David J. Kappos
*Director of the United States Patent and Trademark Office*